US 9,829,312 B2

(12) United States Patent
Xie

(10) Patent No.: US 9,829,312 B2
(45) Date of Patent: Nov. 28, 2017

(54) CHROMATIC CONFOCAL RANGE SENSOR COMPRISING A CAMERA PORTION

(71) Applicant: Mitutoyo Corporation, Kanagawa-ken (JP)

(72) Inventor: Yong Xie, Redmond, WA (US)

(73) Assignee: Mituloyo Corporation, Kanagawa-ken (JP)

( * ) Notice: Subject to any disclaimer, the term of this patent is extended or adjusted under 35 U.S.C. 154(b) by 347 days.

(21) Appl. No.: 14/795,555

(22) Filed: Jul. 9, 2015

(65) Prior Publication Data

US 2017/0010096 A1    Jan. 12, 2017

(51) Int. Cl.
*G01C 3/08* (2006.01)
*H04N 5/225* (2006.01)
*G06T 5/20* (2006.01)
*G01N 21/00* (2006.01)

(52) U.S. Cl.
CPC ............ *G01C 3/08* (2013.01); *G01N 21/00* (2013.01); *G06T 5/20* (2013.01); *H04N 5/2254* (2013.01); *H04N 5/2256* (2013.01)

(58) Field of Classification Search
CPC ............ G01C 3/08; G01N 21/00; G06T 5/20
USPC ........................................... 356/4.01
See application file for complete search history.

(56) References Cited

U.S. PATENT DOCUMENTS

| 7,477,401 | B2 | 1/2009 | Marx et al. |
| 7,626,705 | B2 | 12/2009 | Altendorf |
| 7,876,456 | B2 | 1/2011 | Sesko |
| 7,990,522 | B2 | 8/2011 | Sesko |
| 8,212,997 | B1 * | 7/2012 | Xie ............... G01B 11/026 356/3 |
| 8,587,772 | B2 | 11/2013 | Sesko et al. |
| 2006/0109483 | A1 | 5/2006 | Marx et al. |

OTHER PUBLICATIONS

Molesini et al., "Pseudocolor Effects of Longitudinal Chromatic Aberration", J. Optics (Paris), 1986, vol. 17, No. 6, pp. 279-282.

* cited by examiner

*Primary Examiner* — Mark Hellner
(74) *Attorney, Agent, or Firm* — Seed IP Law Group LLP

(57) ABSTRACT

A chromatic confocal range sensor optical pen comprises a housing, an in/out optical fiber, a chromatically dispersive lens configuration, a reflected light dividing configuration comprising a lower NA zone and a higher NA zone, and a camera portion. The lens configuration is configured to receive source light from the optical fiber and output focused source light to a workpiece surface with axial chromatic dispersion, and receive reflected light from the workpiece surface and focus at least a portion of the reflected light to the fiber aperture. The reflected light dividing configuration is arranged to divide the reflected light into a measurement portion and an imaging portion. In some embodiments, the lower NA zone directs the imaging portion along an imaging optical path to the image detector, and the higher NA zone directs the measurement portion along a measurement optical path to a point proximate to the fiber aperture.

12 Claims, 5 Drawing Sheets

CHROMATIC CONFOCAL RANGE SENSOR COMPRISING A CAMERA PORTION

BACKGROUND

Technical Field

The invention relates generally to precision measurement instruments, and more particularly to a workpiece camera configuration which may be utilized in an optical pen for chromatic confocal range sensing.

Description of the Related Art

Controlled chromatic aberration techniques may be utilized for distance sensing metrology applications. As described in "Pseudocolor Effects of Longitudinal Chromatic Aberration", G. Molesini and S. Quercioli, *J. Optics (Paris)*, 1986, Volume 17, No. 6, pages 279-282, controlled longitudinal chromatic aberration (also referred to herein as axial chromatic dispersion) may be introduced in an optical imaging system, causing the imaging system focal length to vary with wavelength, which provides means for optical metrology. In particular, a lens can be designed whose back focal length (BFL) is a monotonic function of wavelength. In white light operation such a lens exhibits a rainbow of axially dispersed foci that can be used as a spectral probe for distance sensing applications.

As a further example, U.S. Pat. No. 7,477,401, which is hereby incorporated herein by reference in its entirety, discloses that an optical element having axial chromatic aberration, also referred to as axial or longitudinal chromatic dispersion, may be used to focus a broadband light source such that the axial distance to the focus varies with the wavelength. Thus, only one wavelength will be precisely focused on a surface, and the axial distance or height of the surface determines which wavelength is best focused. Upon reflection from the surface, the light is refocused onto a small detector aperture, such as a pinhole and/or the end of an optical fiber. Upon reflection from a surface, only the wavelength that is well-focused on the surface is well-focused on the pinhole and/or fiber. All of the other wavelengths are poorly focused on the fiber, and so will not couple much power into the fiber. Therefore, the signal level will be greatest for the wavelength corresponding to the height of the object. A spectrometer at the detector measures the signal level for each wavelength, which effectively indicates the height of the object.

Another configuration for a chromatic confocal range sensor is described in commonly assigned U.S. Pat. No. 7,626,705 (the '705 patent) which is hereby incorporated herein by reference in its entirety.

Certain manufacturers refer to a practical and compact optical assembly that is suitable for chromatic confocal ranging in an industrial setting as a chromatic confocal range sensor and/or as an "optical pen." One example of optical pen instruments that measure Z height are those manufactured by STIL, S.A. of Aix-en-Provence, France (STIL S.A.). As a specific example, the STIL optical pen model number OP 300NL measures Z heights and has a 300 micron range.

In measurement operations utilizing a chromatic confocal range sensor or optical pen, alignment of a measurement spot of the chromatic confocal range sensor with a particular small region of a workpiece to be measured may be difficult. Known configurations for doing so are cumbersome and/or expensive. In various applications it would be desirable to provide a more convenient, compact, and fast means for alignment of an optical pen measurement spot with a portion of a workpiece.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A chromatic confocal range sensor optical pen operable to provide an image of a measurement spot or line and the surrounding surface to be measured is disclosed. The chromatic confocal range sensor optical pen comprises a housing, an in/out optical fiber, a chromatically dispersive lens configuration, a reflected light dividing configuration and a camera portion. The in/out optical fiber includes a fiber aperture configured to output source light along a measurement optical path and receive reflected light along the measurement optical path. The chromatically dispersive lens configuration has an optical axis which defines a measurement axis of the chromatic confocal range sensor optical pen. The lens configuration is configured to receive the source light and output focused source light to a workpiece surface with axial chromatic dispersion, and receive reflected light from the workpiece surface and focus at least a portion of the reflected light comprising reflected source light along the measurement optical path to a point proximate to the fiber aperture. The reflected light dividing configuration is arranged to receive the reflected light from the chromatically dispersive lens configuration, and divide the reflected light into a measurement portion and an imaging portion. The camera portion comprises an image detector. The reflected light dividing configuration comprises a lower numerical aperture (NA) zone arranged along the optical axis, and a higher numerical aperture (NA) zone surrounding the lower NA zone. The chromatic confocal range sensor optical pen is configured with one of the lower NA zone and the higher NA zone of the reflected light dividing configuration directing the imaging portion of the reflected light along an imaging optical path to the image detector, and the other of the higher NA zone and the lower NA zone of the reflected light dividing configuration directing the measurement portion of the reflected light along the measurement optical path to the point proximate to the fiber aperture.

In some embodiments, the chromatic confocal range sensor optical pen may be configured with the lower NA zone of the reflected light dividing configuration directing the imaging portion of the reflected light along an imaging optical path to the image detector, and the higher NA zone of the reflected light dividing configuration directing the measurement portion of the reflected light along the measurement optical path to the point proximate to the fiber aperture. Such embodiments are especially advantageous in that higher NA light rays provide better Z height measurement resolution and lower NA light rays provide a higher depth of focus for imaging.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
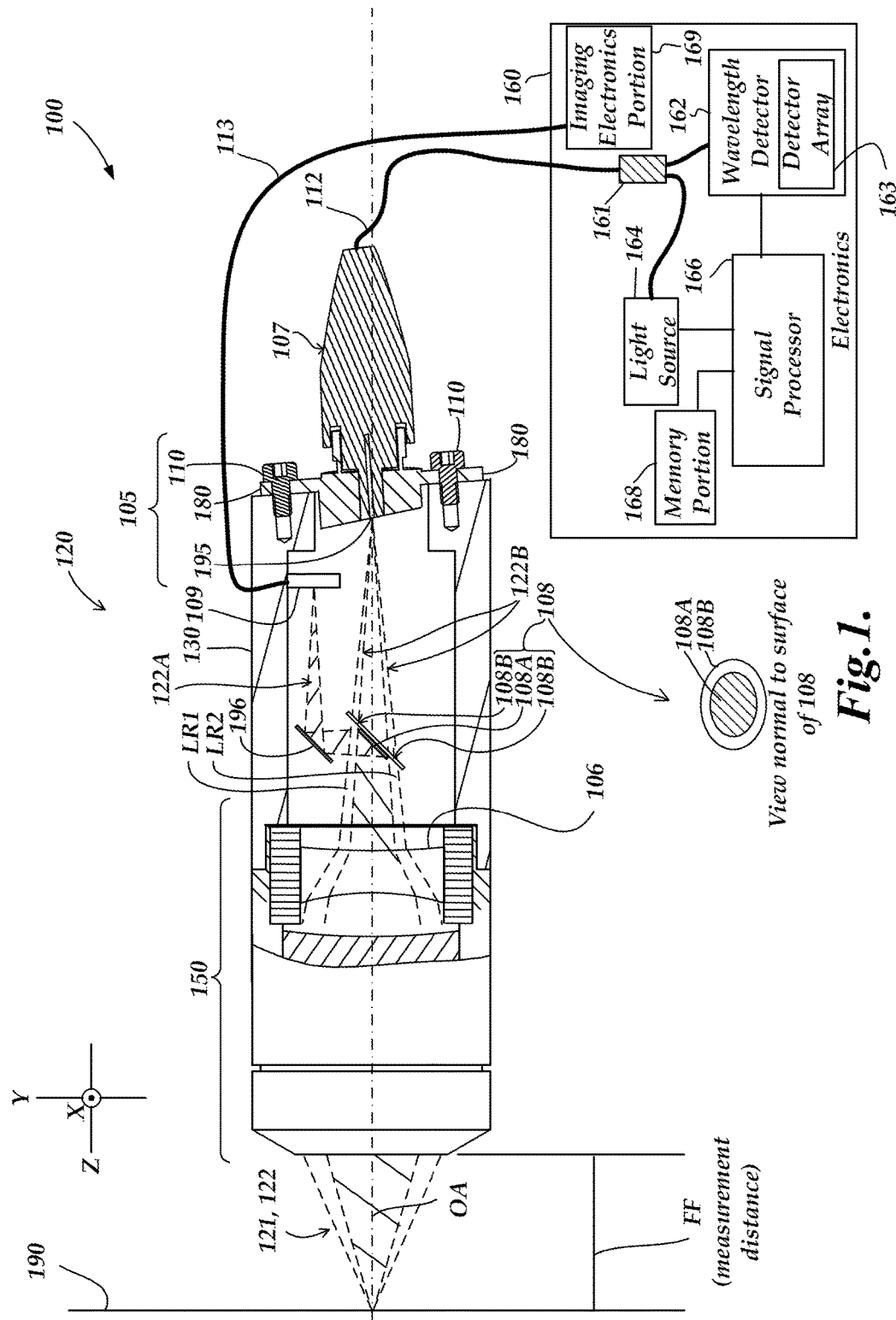
FIG. 1 is a block diagram of an exemplary chromatic confocal range sensor, wherein the optical pen includes a reflected light dividing configuration and a camera portion according to principles disclosed herein.
Figure 2:
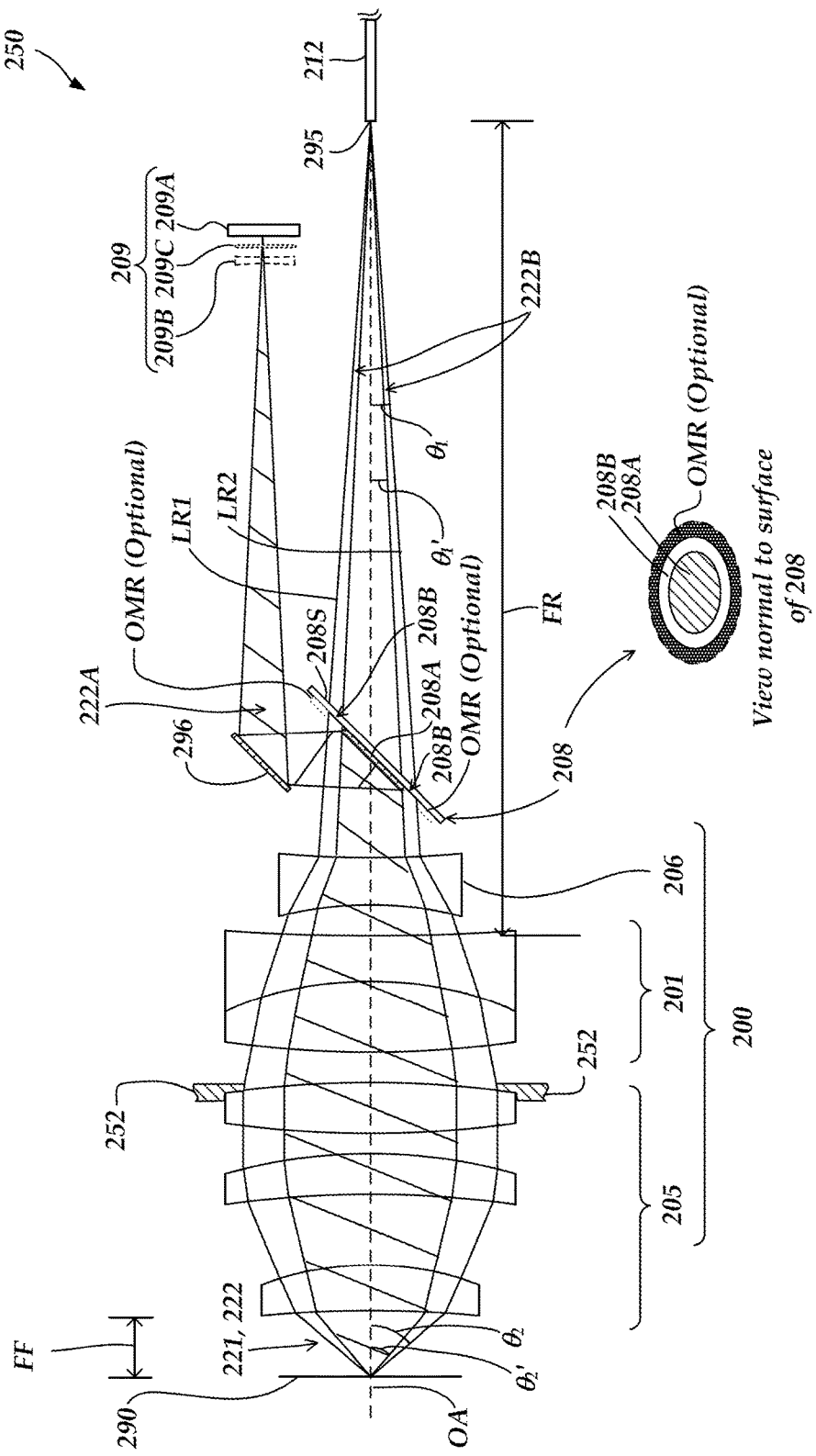
FIG. 2 is a diagram of a schematic side view of the optical paths associated with a first embodiment of a reflected light dividing configuration and a camera portion usable in an optical pen configuration according to principles disclosed herein.

FIG. 1 is a block diagram of an exemplary chromatic confocal range sensor 100. The chromatic confocal range sensor 100 generally corresponds to and may be understood further based on analogous sensors described in U.S. Pat. Nos. 7,876,456 and 7,990,522 which are hereby incorporated herein by reference in their entirety. Briefly, as shown in FIG. 1, the chromatic confocal range sensor 100 includes an optical pen 120 and an electronics portion 160. The optical pen 120 includes an in/out fiber optic sub-assembly 105, a housing 130, an optics portion 150, a reflected light dividing configuration 108 and a camera portion 109. The in/out fiber optic sub-assembly 105 includes a mounting element 180, that may be attached to the end of the housing 130 using mounting screws 110. The optics portion 150 comprises a chromatically dispersive lens configuration having an optical axis OA which defines a measurement axis of the optical pen 120. The in/out fiber optic sub-assembly 105 receives an in/out optical fiber (not shown) through an optical fiber cable 112 which encases it, and through a fiber optic connector 107. The in/out optical fiber outputs source light 121 through a fiber aperture 195 along a measurement optical path, and receives reflected measurement signal light along the measurement optical path through the fiber aperture 195. The optics portion 150 may include an optional telephoto lens 106 which provides a desired level of magnification in a compact arrangement. It should be appreciated that more generally, the optics portion 150 may comprise any desirable combination of lenses according to known optical pen design principles. One exemplary embodiment of an optics portion comprising multiple lenses is shown in FIG. 2.

Generally speaking, the reflected light dividing configuration 108 divides some of the light from the light reflected from the surface to be measured for use as surface imaging light, as described further below, and the remaining light from the reflected light dividing configuration 108 operates as distance measurement light in the optical pen. Regarding distance measurement, the optical pen 120 operates as follows: In operation, broadband (e.g., white) source light 121 emitted from the fiber end through the fiber aperture 195 is focused by the optics portion 150, which includes a lens or lenses that provide an axial chromatic dispersion, such that the focal point along an optical axis OA is at different distances depending on the wavelength of the light, as is known for chromatic confocal sensor systems. The source light 121 includes a wavelength that is focused on a workpiece surface 190. The optics portion 150 is configured to receive the source light 121 and output focused source light 121 to a workpiece surface 190 with axial chromatic dispersion and receive reflected light 122 from the workpiece surface and focus at least a portion of the reflected light 122 comprising reflected source light (e.g., reflected source light in the measurement portion 122B) along the measurement optical path to a point proximate to the fiber aperture 195.

The operative source light 121 and reflected light 122 are bounded by the limiting rays LR1 and LR2. Due to the axial chromatic dispersion, only one wavelength will have a front focus dimension FF that matches the measurement distance from the optical pen 120 to the surface 190. The wavelength that is best focused at the surface 190 will also be the wavelength of the measurement portion 122B of the reflected light 122 that is best focused at the fiber aperture 195. The fiber aperture 195 spatially filters the measurement portion 122B such that predominantly the best focused wavelength passes through the fiber aperture 195 and into the core of the optical fiber cable 112. As described in more detail below and in the incorporated references, the optical fiber cable 112 routes the reflected signal light to a wavelength detector 162 that is utilized for determining the wavelength having the dominant intensity, which corresponds to the measurement distance to the workpiece surface 190.

The reflected light dividing configuration 108 is arranged to receive the reflected light 122 from the optics portion 150, and divide the reflected light 122 into an imaging portion 122A and the measurement portion 122B. The reflected light dividing configuration 108 comprises a lower numerical aperture (NA) zone 108A arranged along the optical axis, and a higher numerical aperture (NA) zone 108B surrounding the lower NA zone. The optical pen 120 is configured with the lower NA zone of the reflected light dividing configuration 108 directing the imaging portion 122A of the reflected light 122 along an imaging optical path to the image detector, and the higher NA zone of the reflected light dividing configuration directing the measurement portion 122B of the reflected light 122 along the measurement optical path to the point proximate to the fiber aperture 195.

In the embodiment shown in FIG. 1, the imaging portion 122A of the reflected light 122 is reflected by a mirror like surface in the lower numerical aperture (NA) zone 108A of the reflected light dividing configuration 108 to a reflector 196 which reflects it to the camera portion 109. The measurement portion 122B of the reflected light 122 is transmitted by a transparent material, or an opening, in the higher numerical aperture (NA) zone 108B of the reflected light dividing configuration 108 to the fiber aperture 195.

The electronics portion 160 includes an optical fiber coupler 161, the wavelength detector 162, a light source 164, a signal processor 166, a memory portion 168 and an imaging electronics portion 169. In various embodiments, the wavelength detector 162 includes a spectrometer or spectrograph arrangement wherein a dispersive element (e.g., a grating) receives the reflected light 122 through the optical fiber cable 112 and transmits the resulting spectral intensity profile to a detector array 163. The wavelength detector 162 may also include related signal processing (e.g., provided by the signal processor 166, in some embodiments) that removes or compensates certain detector-related error components from the profile data. Thus, certain aspects of the wavelength detector 162 and the signal processor 166 may be merged and/or indistinguishable in some embodiments. The imaging electronics portion 169 is configured to receive data from the camera portion 109 through a signal line 113, which may be displayed on a computer monitor or the like.

The white light source 164, which is controlled by the signal processor 166, is coupled through the optical fiber coupler 161 (e.g., a 2×1 optical coupler) to the optical fiber cable 112. As described above, the light travels through the optical pen 120 which produces longitudinal chromatic aberration so that its focal length changes with the wavelength of the light. The wavelength of light that is most efficiently transmitted back through the fiber is the wavelength that is in focus on the surface 190. The reflected wavelength-dependent light intensity then passes through the optical fiber coupler 161 again so that approximately 50% of the light is directed to the wavelength detector 162, which may receive a spectral intensity profile distributed over an array of pixels along a measuring axis of the detector array 163, and operate to provide corresponding profile data. Briefly, a subpixel-resolution distance indicating coordinate of the profile data (e.g., a peak position coordinate) is calculated by the signal processor 166, and the distance indicating coordinate corresponding to the wavelength peak determines the measurement distance to the surface via a distance calibration lookup table which is stored in the memory portion 168. The distance indicating coordinate may be determined by various methods such as determining the centroid of profile data included in a peak region of the profile data.

FIG. 2 is a diagram of a schematic side view of the optical paths associated with a first embodiment of a reflected light dividing configuration 208 and a camera portion 209 usable in an optical pen configuration 250 according to principles disclosed herein. The elements and paths shown in FIG. 2 are functionally analogous to similarly numbered elements in FIG. 1 (e.g., the reflected light dividing configuration 208 is similar to the reflected light dividing configuration 108), and may be similarly understood. Therefore, only certain details are emphasized in the following description, which may be considered supplemental to the description of FIG. 1.

The optical pen configuration 250 includes a lens configuration 200, the reflected light dividing configuration 208 and an in/out optical fiber 212 having a fiber aperture 295. In the embodiment shown in FIG. 2, the lens configuration 200 includes a doublet lens element 201, a positive power lens portion 205 and a telephoto lens 206. However, such an embodiment is exemplary only and not limiting. In operation, broadband source light 221 emitted from the fiber aperture 295 is focused by the lens configuration 200 on a workpiece surface 290. The lens configuration 200 receives reflected light 222 from the workpiece surface 290 and focuses at least a portion of the reflected light 222 to a point proximate to the fiber aperture 295.

The reflected light dividing configuration 208 is located between the lens configuration 200 and the in/out optical fiber aperture 295. The reflected light dividing configuration 208 comprises a lower NA zone 208A and a higher NA zone 208B. In the embodiment shown in FIG. 2, the lower NA zone 208A is a reflective zone and the higher NA zone 208B is a transmissive zone. In some embodiments, such as that shown in FIG. 2, the reflected light dividing configuration 208 may comprise a transmissive substrate 208S, the lower NA zone 208A may comprise a masked reflective region of the transmissive substrate 208S and the higher NA zone 208B may comprise an unmasked region of the transmissive substrate 208S. In other embodiments, the reflected light dividing configuration 208 may comprise a metallic substrate, the lower NA zone 208A may comprise a region suspended within the metallic substrate and the higher NA portion 208B may comprise holes through the metallic substrate. The lower NA zone 208A is shaped as an ellipse and the higher NA zone 208B is shaped as an elliptical annulus in the illustrated embodiment. Their projection along the direction of the optical axis may therefore be circular in this embodiment. However, this configuration is exemplary only, and not limiting. Embodiments which use other zone shapes may still provide benefits similar to those described herein.

During operation, source light from the in/out optical fiber 212 is output from the fiber aperture 295 that is fixed relative to the lens configuration 200 to provide source light along the optical axis OA. In one embodiment, the end of the core of the in/out optical fiber 212 may provide the fiber aperture 295. The source light is directed toward the lens configuration 200 which focuses the source light on the workpiece surface 290. The reflected light from the workpiece surface 290 is refocused by the lens configuration 200 along an optical path that passes back through the reflected light dividing configuration 208 and the measurement portion 222B of the light (transmitted by the higher NA zone 208B) is focused onto a point proximate to (and/or at) the fiber aperture 295. The higher NA zone 208B extends on its outer periphery to the limiting rays LR1 and LR2 which in some embodiments may be limited by an optional outer masking region OMR (shown in dashed outline in FIG. 2). The outer masking region OMR may comprise a light blocking and/or absorbing surface configuration in various embodiments. In other embodiments, the outer masking region OMR may be omitted and a portion of the housing or lens mounting or the like (e.g., the portion 252, shown in FIG. 2) may provide a similar function in that it may be the limiting aperture that bounds the operative reflected light 222. Any light rays in the lower NA zone 208A are directed by mirror surface located in that zone of the reflected light dividing configuration 208 to the reflector 296 as an imaging portion 222A of the reflected light from the surface, which is directed toward the camera portion 209. As previously indicated, light rays between the outer periphery of the lower NA zone 208A and the limiting operative rays LR1 and LR2 are transmitted toward the fiber aperture 295 as a measurement portion 222B of the reflected light. A distance FR represents the spacing between the back of the lens configuration 200 and the fiber aperture 295.

It should be appreciated that in the embodiment shown in FIG. 2, the imaging optical path does not extend beyond a radius of the lens configuration 200 and/or the inner wall of an optical pen housing, in a direction perpendicular to the optical axis OA of the chromatic confocal range sensor optical pen configuration 250. This allows the chromatic confocal range sensor optical pen configuration 250 to have a compact cylindrical shaped housing which contains and protects the entire imaging optical path.

It will be appreciated that light rays in the lower NA zone 208A may comprise rays from ambient light or from auxiliary illumination of the workpiece surface (e.g., from a ring light) from a region surrounding an illumination spot of the optical pen source light, as well as lower NA light rays arising from the optical pen source light. Thus, regions of the workpiece surface outside the source light illumination spot may be imaged.

The camera portion 209 comprises an imaging array 209A. In some embodiments, the camera portion 209 may comprise a field lens 209B in order to suppress field aberration. In some embodiments, the camera portion 209 may comprise a wavelength filter 209C in order to filter wavelengths of the reflected light 222 which are not well focused. The image from the camera portion 209 may be read out and displayed according to known methods.

FIG. 2 shows rear and front convergence/divergence angles $\theta_1$ and $\theta_2$, respectively, associated with the limiting light rays (e.g., LR1 and/or LR2 for the "rear" limiting rays) of the operative measurement portion 222B of the reflected light of the optical pen configuration 250, and the rear and front focus dimensions FR and FF. It will be appreciated that the rear and front focus dimensions FR and FF, will generally depend on the wavelength of light, due to the axial chromatic dispersion provided by the lens configuration 200. The maximum unblocked or open rear numerical aperture higherNArear$_{MAXOPEN}$ related to the higher NA zone 208B is:

$$\text{higherNArear}_{MAXOPEN} = \sin\theta_1 \quad \text{(Eq. 1A)}$$

The minimum unblocked or open rear numerical aperture higherNArear$_{MINOPEN}$ related to the higher NA zone 208B is:

$$\text{higherNArear}_{MINOPEN} = \sin\theta_1' \quad \text{(Eq. 1B)}$$

The maximum unblocked or open front numerical aperture higherNA$_{MAXOPEN}$ related to the higher NA zone 208B is defined as:

$$\text{higherNA}_{MAXOPEN} = \sin\theta_2 \quad \text{(Eq. 2A)}$$

In addition, the minimum unblocked or open front numerical aperture NAfront$_{MINOPEN}$ related to the higher NA zone 208B is defined as:

$$\text{higherNA}_{MINOPEN} = \sin\theta_2' \quad \text{(Eq. 2B)}$$

The portion of light within the angle $\theta_2'$ is the light associated with the lower NA zone 208A of the reflected light dividing configuration 208 that is directed along the workpiece surface and/or spot imaging optical path. Therefore, the maximum unblocked or open front numerical aperture lowerNA$_{OPERATIVE}$ related to the lower NA zone 208A is defined as:

$$\text{lowerNA}_{OPERATIVE} = \sin\theta_2' \quad \text{(Eq. 3)}$$

The rays of the source light which are transmitted by the higher NA portion 208A of the reflected light dividing configuration 208 may be understood to have an effective "average" front numerical aperture higherNA$_{OPERATIVE}$:

$$\text{higherNA}_{OPERATIVE} = (\sin\theta_2 + \sin\theta_2')/2 \quad \text{(Eq. 4)}$$

In various embodiments, it may be advantageous if an optical pen (e.g., the reflected light dividing configuration 208 and other optical elements) is configured such that higherNA$_{OPERATIVE}$ has a value which is at least 1.25, or 1.4, or more, times the value of lowerNA$_{OPERATIVE}$. However, these ratios are exemplary only, and not limiting. More generally, it should be appreciated that due to the operation of the reflected light dividing configuration 208, the operative rays of the measurement portion 222B of the light reflected from the workpiece surface have a higher average numerical aperture than would be the case in the absence of the reflected light dividing configuration 208. This may result in improved workpiece surface position measurement resolution in a chromatic confocal range sensor. A lower numerical aperture may generally be associated with a greater focal depth (e.g., the focal depth associated with a light ray having a corresponding numerical aperture may be qualitatively understood to be related to the known conventional relationship where the depth of field of a lens is inversely proportional to the square of its numerical aperture). Therefore, the imaging portion 222A of the light reflected from the workpiece surface will have a higher depth of field which is advantageous for imaging a surface with a varying height. In some embodiments, this may be as much as a four-fold increase in the depth of field associated with the NA of the light of the imaging portion 222A relative to the NA of the light of the measuring portion 222B, which is a desirable outcome for each of the imaging and measuring functions.

Figure 3:
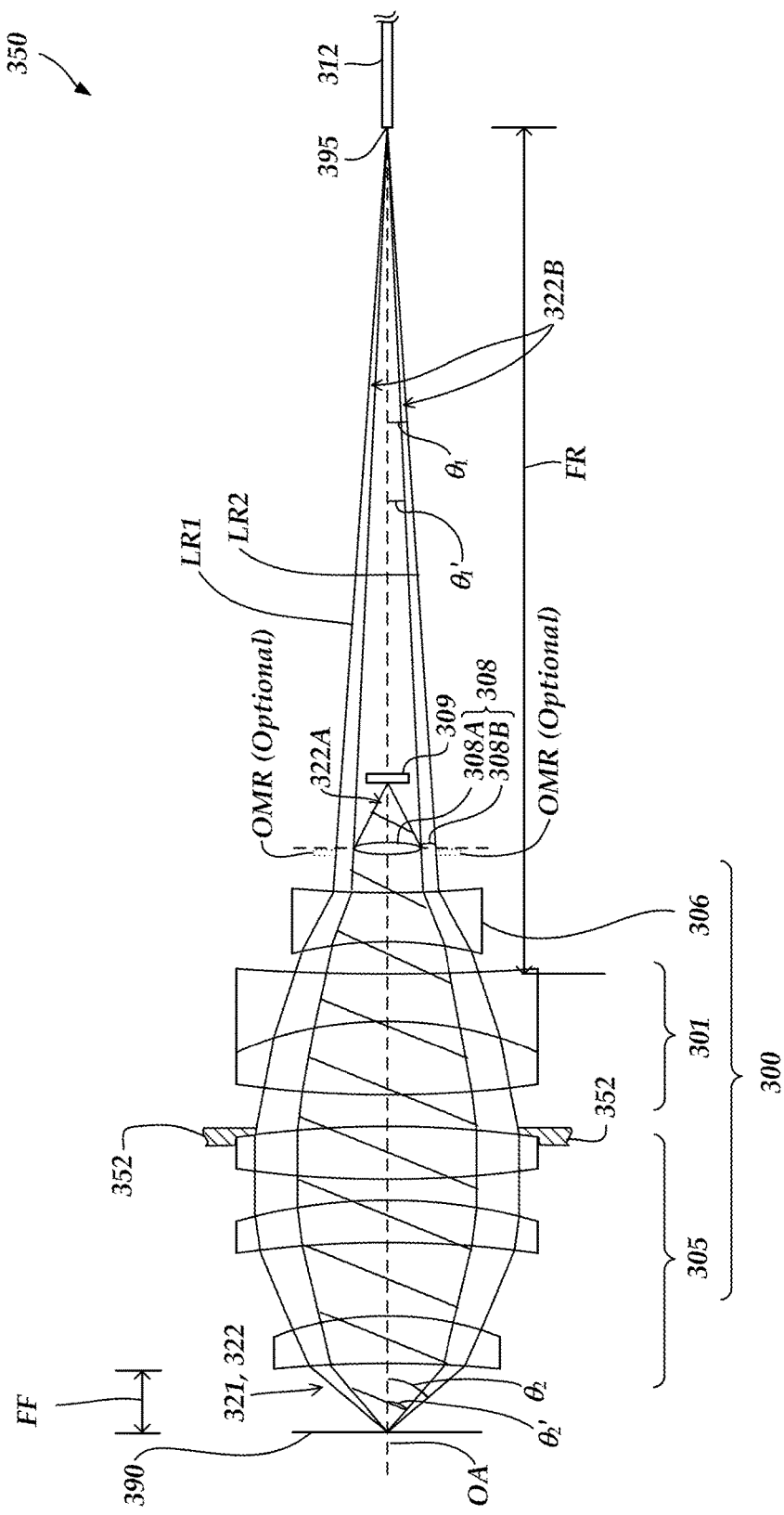
FIG. 3 is a diagram of a schematic side view of the optical paths associated with a second embodiment of a reflected light dividing configuration and a camera portion usable in an optical pen configuration according to principles disclosed herein.

FIG. 3 is a diagram of a schematic side view of the optical paths associated with a second embodiment of a reflected light dividing configuration 308 and a camera portion 309 usable in an optical pen configuration 350 according to principles disclosed herein. Certain elements of the optical pen configuration 350 numbered 3XX may be similar or identical to elements numbered 3XX using similar "XX" numerical suffixes in FIG. 2, and may be understood by analogy.

As shown in FIG. 3, in this embodiment the reflected light dividing configuration 308 comprises a lower NA zone 308A. The lower NA zone 308A in this embodiment comprises a focusing portion which is a lens which collects and focuses the imaging portion 322A of the reflected light. It is surrounded by a higher NA zone 308B which is an annular open or transparent aperture portion. Any light rays in the lower NA zone 308A are focused by lens 308A as an imaging portion 322A of the reflected light to the camera portion 309, and any light rays between the outer periphery of the lower NA zone 308A and the limiting operative rays LR1 and LR2 are transmitted through the higher NA zone 308B toward the fiber aperture 395 as a measurement portion 322B of the reflected light. The lens 308A may be mounted on a transparent element that is attached to the optical pen housing, or may be suspended by narrow supports that do not significantly interfere with the measurement portion 322B of the reflected light, or the like.

Figure 4:
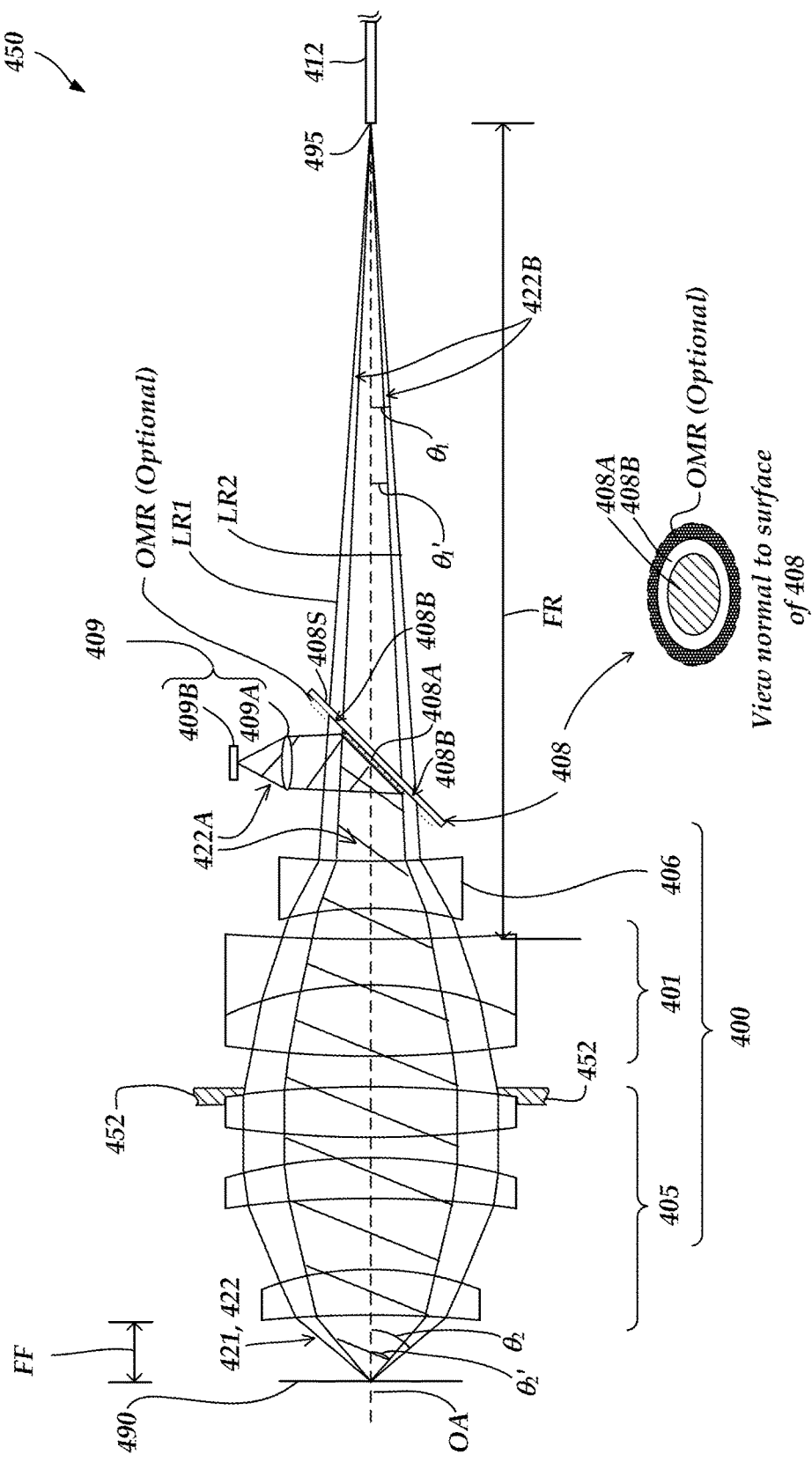
FIG. 4 is a diagram of a schematic side view of the optical paths associated with a third embodiment of a reflected light dividing configuration and a camera portion usable in an optical pen configuration according to principles disclosed herein.

FIG. 4 is a diagram of a schematic side view of the optical paths associated with a third embodiment of a reflected light dividing configuration 408 and a camera portion 409 usable in an optical pen configuration 450 according to principles disclosed herein. Certain elements of the optical pen configuration 450 numbered 4XX may be similar or identical to elements numbered 4XX using similar "XX" numerical suffixes in FIG. 2 and/or FIG. 3, and may be understood by analogy. As shown in FIG. 4, the reflected light dividing configuration 408 comprises a lower NA zone 408A and a higher NA zone 408B. In some embodiments, the reflected light dividing configuration 408 may be similar or identical to the reflected light dividing configuration 208 shown in FIG. 2. The camera portion 409 comprises a field lens 409A and an imaging array 409B. The field lens 409A allows for a more compact configuration which may be suitable to fit inside a cylindrical housing of the optical pen configuration 450.

As shown in FIG. 4, any light rays incident on the lower NA zone 408A are reflected to the camera portion 409 as an imaging portion 422A and any light rays between the outer periphery of the lower NA zone 408A and the limiting operative rays LR1 and LR2 are transmitted through the higher NA portion 408B toward the fiber aperture 495 as a measurement portion 422B.

Figure 5:
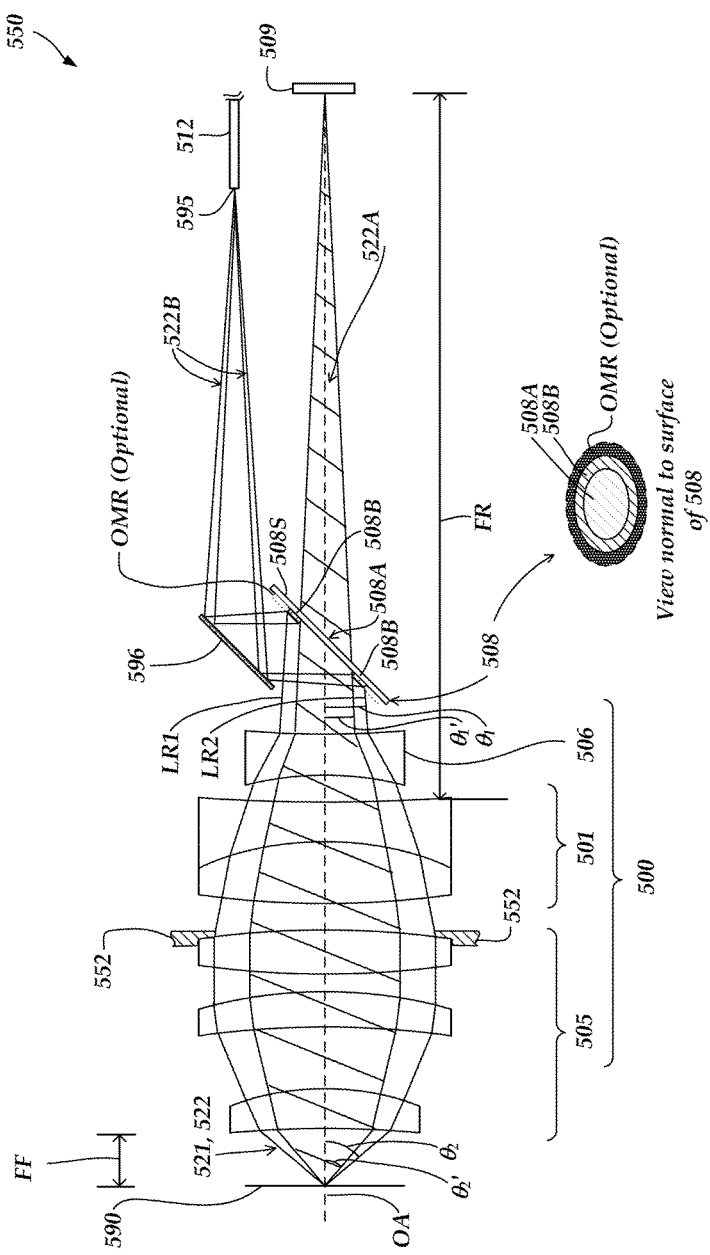
FIG. 5 is a diagram of a schematic side view of the optical paths associated with the optical paths associated with a fourth embodiment of a reflected light dividing configuration and a camera portion usable in an optical pen configuration according to principles disclosed herein.

FIG. 5 is a diagram of a schematic side view of the optical paths associated with a fourth embodiment of a reflected light dividing configuration 508 and a camera portion 509 usable in an optical pen configuration 550 according to principles disclosed herein. Certain elements of the optical pen configuration 550 numbered 5XX may be similar or identical to elements numbered 5XX using similar "XX" numerical suffixes in FIG. 2, and may be understood by analogy.

In comparison to the previously described embodiments, the reflected light dividing configuration 508 comprises a lower NA zone 508A and a higher NA zone 508B which are "reversed" in terms of their reflective and transmissive properties, and which therefore cause the imaging and measuring optical paths to be "reversed" as well. More specifically, as will be understood by one of ordinary skill in the art based on this disclosure, any light rays between the outer periphery of the lower NA zone 508A and the limiting operative rays LR1 and LR2 are reflected toward a reflector 596 where they are reflected toward a fiber aperture 595 that is "off center" in the optical pen, as a measurement portion 522B of the reflected light. Any light rays in the higher NA zone 508B are transmitted by the reflected light dividing configuration 508 as an imaging portion 522B of the reflected light, to the camera portion 509.

While the preferred embodiments of the invention have been illustrated and described, numerous variations in the illustrated and described arrangements of features and sequences of operations will be apparent to one skilled in the art based on this disclosure. For example, a chromatic confocal range sensor including an optical pen has been shown herein. However, a chromatic confocal range sensor such as a chromatic line sensor, may be configured to operate according to the systems and methods disclosed herein. Thus, it will be appreciated that various changes can be made to embodiments disclosed herein without departing from the spirit and scope of the invention.

The embodiments of the invention in which an exclusive property or privilege is claimed are defined as follows:

1. A chromatic confocal range sensor optical pen operable to provide an image of a measurement spot on a workpiece surface to be measured, the chromatic confocal range sensor optical pen comprising:
   a housing;
   an in/out optical fiber including a fiber aperture configured to output source light along a measurement optical path and receive reflected light along the measurement optical path;
   a chromatically dispersive lens configuration having an optical axis which defines a measurement axis of the chromatic confocal range sensor optical pen, the lens configuration configured to:
      receive the source light and output focused source light to a workpiece surface with axial chromatic dispersion; and
      receive reflected light from the workpiece surface and focus at least a portion of the reflected light comprising reflected source light along the measurement optical path to a point proximate to the fiber aperture;
   a reflected light dividing configuration arranged to receive the reflected light from the chromatically dispersive lens configuration, and divide the reflected light into a measurement portion and an imaging portion; and
   a camera portion comprising an image detector,
   wherein:
      the reflected light dividing configuration comprises a lower numerical aperture (NA) zone arranged along the optical axis, and a higher numerical aperture (NA) zone surrounding the lower NA zone; and
      the chromatic confocal range sensor optical pen is configured with one of the lower NA zone and the higher NA zone of the reflected light dividing configuration directing the imaging portion of the reflected light along an imaging optical path to the image detector, and the other of the higher NA zone and the lower NA zone of the reflected light dividing configuration directing the measurement portion of the reflected light along the measurement optical path to the point proximate to the fiber aperture.

2. The chromatic confocal range sensor optical pen of claim 1, wherein one of the lower NA zone and the higher NA zone is a reflective zone and the other is a transmissive zone.

3. The chromatic confocal range sensor optical pen of claim 2, wherein the chromatic confocal range sensor optical pen is configured with the lower NA zone of the reflected light dividing configuration directing the imaging portion of the reflected light along an imaging optical path to the image detector, and the higher NA zone of the reflected light dividing configuration directing the measurement portion of the reflected light along the measurement optical path to the point proximate to the fiber aperture.

4. The chromatic confocal range sensor optical pen of claim 1, wherein the imaging optical path is contained in the housing and within a radius of the chromatically dispersive lens configuration in a direction perpendicular to the optical axis of the chromatic confocal range sensor optical pen.

5. The chromatic confocal range sensor optical pen of claim 1, wherein the reflected light dividing configuration comprises a transmissive substrate, the lower NA zone comprises a masked reflective region of the transmissive substrate and the higher NA zone comprises an unmasked region of the transmissive substrate.

6. The chromatic confocal range sensor optical pen of claim 1, wherein the reflected light dividing configuration is located between the chromatically dispersive lens configuration and the in/out optical fiber.

7. The chromatic confocal range sensor optical pen of claim 1, wherein the reflected light dividing configuration comprises a metallic substrate, the lower NA zone comprises a region suspended within the metallic substrate and the higher NA portion comprises holes through the metallic substrate.

8. The chromatic confocal range sensor optical pen of claim 1, wherein the camera portion comprises a wavelength filter.

9. The chromatic confocal range sensor optical pen of claim 1, wherein the camera portion comprises a field lens proximate to the imaging portion.

10. The chromatic confocal range sensor optical pen of claim 1, wherein the chromatic confocal range sensor optical pen is configured with the lower NA zone of the reflected light dividing configuration directing the imaging portion of the reflected light along an imaging optical path to the image detector, and the higher NA zone of the reflected light dividing configuration directing the measurement portion of the reflected light along the measurement optical path to the point proximate to the fiber aperture.

11. The chromatic confocal range sensor optical pen of claim 10, wherein the lower NA zone comprises a focusing portion.

12. The chromatic confocal range sensor optical pen of claim 1, wherein the chromatic confocal range sensor optical pen is configured with the higher NA zone of the reflected light dividing configuration directing the imaging portion of the reflected light along an imaging optical path to the image detector, and the lower NA zone of the reflected light dividing configuration directing the measurement portion of the reflected light along the measurement optical path to the point proximate to the fiber aperture.

\* \* \* \* \*

UNITED STATES PATENT AND TRADEMARK OFFICE
CERTIFICATE OF CORRECTION

PATENT NO. : 9,829,312 B2  
APPLICATION NO. : 14/795555  
DATED : November 28, 2017  
INVENTOR(S) : Yong Xie Page 1 of 1

It is certified that error appears in the above-identified patent and that said Letters Patent is hereby corrected as shown below:

On the Title Page

Item (73) Assignee:
"Mituloyo Corporation, Kanagawa-ken (JP)" should read, --Mitutoyo Corporation, Kanagawa-ken (JP)--.

Signed and Sealed this  
Seventh Day of August, 2018

Andrei Iancu  
*Director of the United States Patent and Trademark Office*